(12) United States Patent
Bray et al.

(10) Patent No.: US 9,763,991 B2
(45) Date of Patent: Sep. 19, 2017

(54) COMPOSITION FOR THE TREATMENT OF NEUROBEHAVIORAL DISORDERS

(71) Applicant: Cannabis Science International Holding B.V., Haarlem (NL)

(72) Inventors: Dorothy Helen Bray, Buckinghamshire (GB); Mario Lap, Amsterdam (NL); Alfredo Carlos Dupetit, Neunkirchen-Richelbach (DE)

(73) Assignee: CANNABIS SCIENCE INTERNATIONAL HOLDING B.V., Haarlem (NL)

( * ) Notice: Subject to any disclaimer, the term of this patent is extended or adjusted under 35 U.S.C. 154(b) by 0 days.

(21) Appl. No.: 14/898,251

(22) PCT Filed: Jun. 13, 2014

(86) PCT No.: PCT/NL2014/050391
§ 371 (c)(1),
(2) Date: Dec. 14, 2015

(87) PCT Pub. No.: WO2014/200350
PCT Pub. Date: Dec. 18, 2014

(65) Prior Publication Data
US 2016/0129060 A1    May 12, 2016

(30) Foreign Application Priority Data

Jun. 13, 2013  (NL) .................................... 2010968

(51) Int. Cl.
| | |
|---|---|
| A01N 65/00 | (2009.01) |
| A61K 36/185 | (2006.01) |
| A61K 31/05 | (2006.01) |
| A61K 31/352 | (2006.01) |
| A23L 2/52 | (2006.01) |
| A23L 33/105 | (2016.01) |
| A61K 36/752 | (2006.01) |

(52) U.S. Cl.
CPC .............. *A61K 36/185* (2013.01); *A23L 2/52* (2013.01); *A23L 33/105* (2016.08); *A61K 31/05* (2013.01); *A61K 31/352* (2013.01); *A23V 2002/00* (2013.01); *A61K 36/752* (2013.01); *A61K 2236/15* (2013.01)

(58) Field of Classification Search
CPC ...................................................... A61K 36/00
USPC ......................................................... 424/725
See application file for complete search history.

(56) References Cited

U.S. PATENT DOCUMENTS 6,630,507 B1    10/2003   Hampson et al.

FOREIGN PATENT DOCUMENTS

WO          9953917 A1    10/1999

OTHER PUBLICATIONS

Anonymous, "How Do THC, CBN, and CBD Relate to Marijuana Potency?", http:f/web.archive.orgfweb/20121016065048/http:ffgrowweedeasy.com/thc-cbd-cbn-when-to-harvest-marijuana, (Oct. 2012).
A. C. Campos et al., "Multiple mechanisms involved in the large-spectrum therapeutic potential of cannabidiol in psychiatric disorders", Experientia, pp. 1898-3378, vol. 37. No. 18 (Oct. 2012).
Herring et al.,"Inhibition of the cyclic AMP signaling cascade and nuclear factor binding to CRE and kappaB elements by cannabinol. a minimally CNS-active cannabinoid.", Biochemical Pharmacology, pp. 1013-1023, vol. 55, No. 7(Apr. 1998).
Amy C Herring et al.,"Cannabinol-Mediated Inhibition of Nuclear Factor-kB cAMP Response Element Binding Protein. and Interleukin-2 Secretion by Activated Thymocytes",The Journal of Pharmacology and Experimental Therapeutics, pp. 1156-1163, vol. 291. No. 3 (Dec. 1999).
Giovanni Appendino et al.,"Antibacterial cannabinoids from Cannabis sativa: a structure-activity study" Journal of Natural Products, American Chemical Society, pp. 1427-1430, vol. 71, No. 8 (Aug. 2008).
P. Robson., "Therapeutic aspects of cannabis and cannabinoids", The British Journal of Psychiatry, pp. 187-115, vol. 178, No. 2, (Feb. 2001).

*Primary Examiner* — Michael Meller
(74) *Attorney, Agent, or Firm* — Browdy and Neimark, PLLC

(57) ABSTRACT

The invention relates to a composition for use in the treatment of neurobehavioral disorders, a *Cannabis* plant extract comprising Cannabinol preferably with other constituents of this plant for such use and a method for the extraction of plants. The plants or plant parts may for instance be derived from *Cannabis sativa* and/or *Cannabis indica* and/or *Cannabis ruderalis* and/or citrus fruits, and mixtures thereof. The plant extracts derived showed particularly beneficial effects against sleeping disorders, in particular insomnia, and anxiety disorders including ADHD.

6 Claims, 1 Drawing Sheet

COMPOSITION FOR THE TREATMENT OF NEUROBEHAVIORAL DISORDERS

FIELD OF THE INVENTION

The invention relates to a composition for use in the treatment of neurobehavioral disorders. The invention further relates to a plant extract comprising Cannabinol for use in the treatment of neurobehavioral disorders. The invention further relates to a method for the extraction of plants.

BACKGROUND OF THE INVENTION

*Cannabis* is a very rapidly growing plant, attaining a usual height of three to twenty feet at maturity. *Cannabis* is dioecious, which means that there are sexually distinct male and female plants. The known species are *Cannabis* sativa, *Cannabis indica* and *Cannabis ruderalis* with multiple strains in cultivation.

*Cannabis* use for medicinal purposes dates back at least 3,000 years. It was introduced into Western medicine in the 1840s by W. B. O'Shaughnessy, a surgeon who learned of its medicinal properties while working in India for the British East Indies Company. In most countries, growth and use of *Cannabis* plants is restricted due to the presence of the psychoactive compound tetrahydrocannabinol (THC), along with a plethora of other cannabinoid compounds, terpenes and phenols that do not necessarily share THC's psychoactive effects. The use of *Cannabis* is prohibited in many countries as it is considered a drug due to its psychoactive constituent THC.

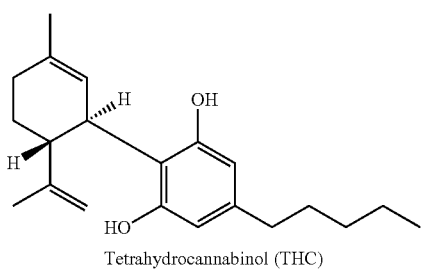 [SMILES: C=C(C)[C@@H]1CCC(C)=C[C@H]1c1c(O)cc(CCCCC)cc1O]

Tetrahydrocannabinol (THC)

Some medical uses of *Cannabis* extracts and isolated compounds are recognized in published peer reviewed literature, as shown in the reference list below, and continue to stimulate increased interest among physicians and patients for multiple medical applications. For instance, cannabis extracts are included in a SATIVEX product approved by regulatory authorities in UK, Spain, New Zealand and Canada to treat spasticity in multiple sclerosis (http://www.gwpharm.com/Sativex.aspx).

U.S. Pat. No. 6,630,507 patent from National Institutes of Health (Hampson et al) describes *Cannabis* spp. isolated compounds called cannabinoids that have antioxidant La properties, and mentions possible use in the treatment of ischemic, age-related, inflammatory and autoimmune diseases. The cannabinoids are said to have particular applications as neuroprotectants, for example in limiting neurological damage following ischemic insults, such as stroke and trauma, or in the treatment of neurodegenerative diseases, such as Alzheimer's disease, Parkinson's disease and HIV related dementia. Cannabidiol is mentioned in particular, as it lacks the toxic and psychoactive effects of THC.

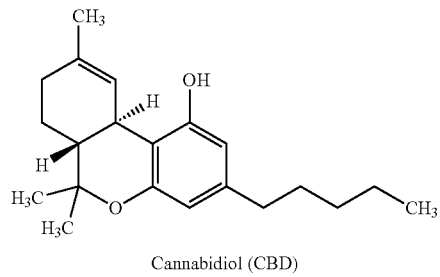 [SMILES: CCCCCc1cc(O)c2c(c1)OC(C)(C)[C@@H]1CCC(C)=C[C@@H]21]

Cannabidiol (CBD)

OBJECT AND SUMMARY OF THE INVENTION

It is an object of the invention to provide new medicinal uses of *Cannabis* plant extracts and cannabinoids.

As a serendipitous discovery, it was found that extracts from *Cannabis sativa* extract prepared in a particular manner (harvested after fruits have formed, dried and extracted using ethanol, with ethanol evaporated) have a positive effect on a number of common neurobehavioral disorders. Plants may be extracted using various solvents with preferably but not exclusively ethyl alcohol as an extraction solvent. The extract may be used as such, or may be processed into liquid or solid formulations, such as tonics, powders, tablets and capsules. The extract is preferably administered orally or delivered directly to the mucosa using acceptable methods of delivery.

The invention provides a composition for use in the treatment of neurobehavioral disorders, including treatment for insomnia wherein the composition comprises a plant extract comprising Cannabinol and other natural constituents contained in *Cannabis* plants extract as prepared above.

The invention relates to a composition for use in the treatment of neurobehavioral disorders, plant extracts obtained from preferably but not exclusively from *Cannabis* spp. comprising preferably but not exclusively Cannabinol and other naturally occurring constituents for such use. The invention also describes method to prepare Cannabinol—rich plant derived composition, said composition containing naturally extracted Cannabinol (or enriched with synthetic Cannabinol) and terpens and/or phenols preferably but not necessarily obtained from *Cannabis* spp.

DETAILED DESCRIPTION OF THE INVENTION

Figure 1:
FIG. 1 shows the measurement of the distance from the oral cavity to the end of the xyphoid process with a feeding needle on the outside of a restrained animal, prior to performing an oral dosing procedure.

As a serendipitous discovery, it was found that extracts from plants other than the *Cannabis* plants, in particular Citrus plant extracts and isolates, with relatively high Cannabinol content have a positive effect on a number of common neurobehavioral disorders. Plants may be extracted using various solvents with ethyl alcohol is a preferred extraction solvent. The extract may be used as such, or may be processed into liquid or solid formulations, such as tonics, powders, tablets and capsules. The extract is preferably administered orally.

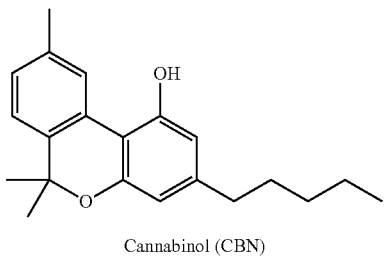 [SMILES: CCCCCc1cc(O)c2c(c1)OC(C)(C)c1ccc(C)cc1-2]

Cannabinol (CBN)

Preferably, the plant extract comprises at least 80% w/w Cannabinol preferably but not exclusively combined with other constituents from *Cannabis* plants. As a preferred plant source, the extract is derived as a plant extract of *Cannabis sativa* and/or *cannabis indica*. As an alternative source, the extract may be derived as a plant extract or isolated from a citrus fruit, preferably *Citrus sinensis* (oranges). For citrus fruits including oranges, the extract is preferably derived from the peel of the fruit. Besides Cannabinol, the extract may contain other compounds, including other cannabinoids, The composition may further comprise terpenes and phenols, in particular terpenes and phenols derived from *Cannabis sativa* and/or *Cannabis indica* and/or *Cannabis* ruderalis.

It is preferred if the amount of psychoactive cannabinoids in the composition is below a is predetermined threshold for having a psychoactive effect. For the beneficial effect on neurobehavioral disorders, the psychoactive effect related to cannabinoids such as THC is regarded as an undesirable side effect. Cannabinol is described by the state of art as not having a psychoactive effect.

Preferably, the composition is essentially free of tetrahydroCannabinol (THC). In view of the invention, compositions are regarded as free of tetrahydrocannabinol if they comprise THC levels of 0.2% w/w or lower.

The plant extract as described herein show a particularly beneficial relief if the neurobehavioral disorder is a sleep disorder. The extracts are effective against various sleep disorders, including types of insomnia such as acute and chronic insomnia.

The extract as described herein is also effective against anxiety disorders. Anxiety disorders on which the extracts have a beneficial effect include the attention deficit hyperactivity disorder (ADHD).

Preferably, the composition is an oral composition, preferably a liquid, a powder or a tablet or a composition that can be delivered to the mucosal tissues using optimal methods of delivery that are available in the state of art. Such formulations may be prepared using physiologically acceptable excipients, including liquid or solid carrier. The extract may also be included in food compositions. Other formulations such a patch or systemic delivery may be acceptable in treating particular medical conditions Preferably, the composition comprises at least one flavoring agent masking the taste of Cannabinol. Suitable masking agents for the taste of Cannabinol include preferably but not exclusively citrus flavours such as orange, lemon and grapefruit, with or without additional sweeteners.

Such composition will be suitable to be used in food products and drinks.

The invention further provides a plant extract comprising Cannabinol for use in the treatment of neurobehavioral disorders.

The invention also provides synthetic cannabinol formulated with at least one terpene and/or phenol, preferably isolated from a *Cannabis* plant, and optionally with other excipients, for use in the treatment of neurobehavioral disorders.

The invention also provides a method for the extraction of plants, comprising the steps of
a) Providing of plants or plant parts with said activity
b) Providing of plants or plant parts with said activity comprising Cannabinol;
c) Letting the plant mature till fruits are obtained
d) Drying of the plants or plant parts to obtain dried plant material
e) Grinding of the plant parts to obtain plant powder
d) Extraction of the plant powder using an extraction solvent to obtain a plant extract; and
e) Optionally evaporating the extraction solvent to obtain a concentrated plant extract.
f) Optionally enriched the plant extract with naturally isolated or synthetic Cannabinol The plants or plan parts may for instance be derived from *Cannabis sativa* and/or *Cannabis indica* or *Cannabis ruderalis* and/or citrus fruit such as *Citrus sinensis*, and mixtures thereof. The drying and grinding may be done using regular laboratory or industrial equipment. For the extraction, preferably organic solvents are used. Ethyl alcohol was shown to be a particularly suitable extract. The extraction solvent may be removed by evaporation to leave a sticky concentrated extract. The concentrated extract may be further purified using techniques such as washing, recrystallization, chromatography, distillation (either regular distillation, vacuum distillation or steam distillation), sublimation, hot air extraction or combinations thereof.

EXAMPLES

Example 1. *Cannabis* Extract

The mode of preparation of the material was perceived to be sufficient to obtain a CBN-rich extract. Fully grown mature *Cannabis sativa* plants were harvested later than normal (with fruits). The late-harvested plants contain a relatively high content of Cannabinol (CBN) and a reduced amount of the psychoactive tetrahydrocannabinol (THC) compared to earlier-harvested *cannabis* plants. In state of art *cannabis* extract producers would carefully control the time of harvest, the storage and extraction method to avoid loss of THC. Extract preparation to obtain CBN requires different conditions and it is not an accidental by-product of THC rich extract production.

Earlier harvested plants contain more THC and less CBN. The THC content can be reduced by further chemical purification techniques to a level where a typical dose by ingestion does not display the undesirable psychoactive effect related to THC. Known purification techniques for cannabinoids include the chromatography, extraction, recrystallization, vacuum distillation and sublimation.

The plants where dried under reduced pressure at 45 degrees for over 4 hours until the machine indicator showed that the material was fully dried and the amount of water still remaining in the plants was under 5%. Subsequently, the dried batch of plants was powdered and alcohol extracted, and the alcohol content was reduced by evaporation under reduced pressure to obtain a sticky concentrated extract.

Chemical analysis has shown that in the plant material contained a high content (>80%) of a non-psychoactive chemical constituent, Cannabinol, among other cannabinoids, terpenes and phenols. Methods for analysis can be found for instance in Mahadevan A, Siegel C, Martin B R, Abood M E, Beletskaya I, Razdan R K (October 2000). "Novel Cannabinol probes for CB1 and CB2 cannabinoid receptors". Journal of Medical Chemistry 43 (20): 3778-85.

Example 2: Treatment of Insomnia with *Cannabis* Extract

Approximately 25 mg of the *cannabis* extract according to example 1 was ingested by a 28 years old male with the intent of recreational use, but the effect was unexpected: instead of the usual THC associated effect, the so-called high, intensification of sensation and increased clarity of perception, the ingestion resulted in relaxation and 6-8 h sleep perceived as very comfortable.

The same extract was subsequently used by six males:
1. Male: 43 (with chronic insomnia) (twice)
2. Male: 52 (twice)
3. Male: 50 (has chronic insomnia) (twice)
4. Male: 45 one time
5. Male: 49 (acute insomnia) one time
6. Male: 73 (chronic insomnia) one time The results indicated that the extracts derived from *Cannabis* having a relatively high amount of the non-psychoactive Cannabinol have a potent sleep inducing effect, counteracting successfully pre-existing insomnia.

Example 3: Treatment of Insomnia with Purified Cannabinol

When pure Cannabinol was obtained using regular chemical laboratory synthesis, a similar effect of relaxation and good quality sleep were obtained when such compound was ingested by five male volunteers suffering from insomnia. Each test subject ingested the substance once at a dose of 20 mg cannabinol. The effect was perceived to have similar efficacy by the volunteer who had also ingested the extract as described in example 1.

This result indicates that Cannabinol has a strong effect in the treatment of insomnia, although it is possible other compounds in the extract also contribute to the effect. As a second conclusion, it is shown that the desired effect is independent of the presence of the psychoactive components of *cannabis*, in particular not dependent on THC.

Example 4: Treatment of Anxiety and ADHD

The effect of the extract according to example 1 included one male subject, age 49 suffering from mild anxiety disorder. This subject ingested once the *cannabis* extract according to example 1 in a dose comprising approximately 25 mg of the extract, and indicated a lowering of anxiety, with an improved mental and physical control. This data would suggest that the said extract is applicable not just in treating anxiety but will also be useful in managing attention deficit disorder (ADHD) symptoms.

Example 5: Oral Dosing (Gavage) of Cannabinol (Range 0.01-0.5 mg/Kg Daily) in C57BL6 Mice Preface Cannabinol is a carbon-containing terpenophenolic compound produced uniquely by *Cannabis* species (e.g., *Cannabis sativa* L.). Cannabinol (CBN) is suspected to have significant analgesic and anti-inflammatory action. Moreover, being delta-9-THC the main component of *Cannabis sativa* L. with psychoactive effect (high), the psychoactive effects of CBN are expected to be minimal, thus making this compound potentially useful as treatment for a variety of diseases or conditions. However, conditions for optimal administration are still unclear.

The experiment is designed to test a range of concentrations around the equivalent previously tested in humans for single-dose kinetics. Animal experiments were performed following the directive 2010/63/EU on the protection of animals used for scientific purposes.

Mice 6 groups of 5-6 male C57BL6 of approximately 28 g body weight (range 27-30 g) with the use of one cage for 3 mice: Group 0: Pure Olive Oil, Group 1: CBN at 0.01 mg/Kg body weight, Group 2: CBN at 0.05 mg/Kg body weight, Group 3: CBN at 0.1 mg/Kg body weight, Group 4: CBN at 0.25 mg/Kg body weight and Group 5: CBN at 0.50 mg/Kg body weight Materials Correctly sized feeding needles (see chart below)

| Mouse weight | Gauge (G) | Length (inch) | Ball Diameter (mm) |
|---|---|---|---|
| 25-32 g | 18 | 2 | 2.25 |

Appropriate sized syringes

Sterilized glass Volumetric flasks (1×50 ml, 1×20 ml, 2×10 ml, 3×5 ml)

Magnetic stirrer

Sterilized stir bar

Pure Cannabinol (stored at −4° C.) obtained from THC Pharm GmbH

Olive oil for human consumption (minimum 750 ml)

Sterile Eppendorf vials 0.5-1.5 ml

Sterile Falcon Vials (10 mL)

Appropriate Pipettes and tips 2 empty cages to allocate mouse temporarily during the gavage procedure Preparation of the Solutions Solutions (named CBN 0, CBN 1, CBN 2, CBN 3, CBN 4, CBN 5, Pure Olive Oil) having different cannabinol concentrations dissolved in olive oil were prepared in sterile conditions, under a laminar flood hood. Pure olive oil was used as a negative control.

Instruction to prepare CBN 0 (5 mg/ml): Weight 50 mg Cannabinol over an aluminium foil. Carefully dispense the 50 mg in a 10 ml glass volumetric flask and add 10 mL of olive oil. Use a sterile magnetic stirrer to allow complete dissolution.

Instruction to prepare CBN 1-5 and Pure Olive Oil: Follow the instruction in Table 1 to prepare CBN1-5 by diluting the appropriate CBN solution. Prepare CBN 1 in the 20 ml volumetric flask; CBN 2, CBN 3 and CBN 5 in the 5 ml volumetric flask; CBN 4 in the 10 ml volumetric flask. Dispense Pure olive Oil in the 50 ml volumetric flask.

TABLE 1

Instruction to prepare solutions CBN 1-5

| Name of the Solution | CBN Concentration (mg/mL) | General Instructions to prepare CBN 1-5 | Volume CBN 0 (mL) | Volume CBN 1 (mL) | Volume CBN 4 (mL) | Volume Olive oil (mL) | Final Volume (mL) |
|---|---|---|---|---|---|---|---|
| CBN 1 | 0.5 | Dilute 2 ml CBN 0 in olive oil (1:10) | 2 | — | — | 18 | 20 |
| CBN 2 | 0.25 | Dilute 2.5 ml CBN 1 in olive oil (1:2) | — | 2.5 | — | 2.5 | 5 |
| CBN 3 | 0.1 | Dilute 1 mL CBN 1 in olive oil (1:5) | — | 1 | — | 4 | 5 |
| CBN 4 | 0.05 | Dilute 1 ml CBN 1 in olive oil (1:10) | — | 1 | — | 9 | 10 |
| CBN 5 | 0.01 | Dilute 1 ml CBN 4 in olive oil (1:5) | — | — | 1 | 4 | 5 |
| Pure Olive Oil (POO) | 0 | — | — | — | — | 5 | 50 |

Procedure

The volume that can be administered to the animal should not exceed 10 ml/kg. For a mouse of 20 g the maximum volume corresponds to 0.2 ml. For this procedure a volume of 0.1 ml will be used (half of the maximum volume). 1 ml of each stock solution (cannabinol, CBN 1-5 and pure olive oil, POO) was dispensed into Falcon vials. Prior to the administration, the weight of each mouse was recorded and the appropriate amount of cannabinol solution was determined. For the POO group always 0.1 ml was dispensed in 6 an eppendorf vessel, for the other experimental groups transfer the amounts of CBN 1-5 and POO according to table 2 were used in an eppendorf vial. The amounts to be administered were adjusted depending on mouse group and individual weights.

TABLE 2

Amount of CBN 1-5 and POO to be mixed prior administration to each mouse group.

| Mouse group | CBN 1 (ml) | CBN 2 (ml) | CBN 3 (ml) | CBN 4 (ml) | CBN 5 (ml) | POO (ml) | Total (ml) |
|---|---|---|---|---|---|---|---|
| Group 1 (0.01 mg/kg) | | | | | 0.028 | 0.072 | 0.1 |
| Group 2 (0.05 mg/kg) | | | | 0.028 | | 0.072 | 0.1 |
| Group 3 (0.1 mg/Kg) | | | 0.028 | | | 0,072 | 0.1 |
| Group 4 (0.25 mg/Kg) | | 0.028 | | | | 0.072 | 0.1 |
| Group 5 (0.5 mg/Kg) | 0.028 | | | | | 0.072 | 0.1 |

Administration of the Solution

Use the syringe to aspire 0.1 ml from the prepared solution. Prior to performing the oral dosing procedure, measure the distance from the oral cavity to the end of the xyphoid process (caudal point of the sternum) with the feeding needle on the outside of the restrained animal, as shown in FIG. 1. This will be how far the needle will be inserted into the oesophagus. Do not at any time force the needle down the oesophagus, this may cause tears to the oesophagus, injury to the animal, or you may inadvertently force the needle down the trachea.

Figure 2:
FIG. 2 shows the sliding of the end of the feeding needle attached to the filled syringe along the roof of the animal's oral cavity towards the animal's left side.

With the feeding needle attached to the filled syringe, slide the end of the feeding needle along the roof of the animal's oral cavity towards the animal's left side. The feeding needle should slide down the oesophagus with gravity alone. There should be no resistance when passing the feeding needle (FIG. 2). The gavage needle may rotate clockwise slightly as it passes the epiglottis and into the oesophagus. The animal may gag when the needle is passed; this is normal. If there is any resistance or if the animal struggles excessively remove the feeding needle, ensure you have good restraint on the animal and attempt to pass the needle again.

Figure 3:
FIG. 3 shows the injection of a solution once the feeding needle is in to the premeasured distance.

Once the feeding needle is in to the premeasured distance, slowly inject the solution to minimize the fluid coming back up the oesophagus. There should be no resistance while injecting the needle will be in the distal oesophagus, not the stomach (FIG. 3). Remove the feeding needle in the opposite direction from insertion and return the animal to its cage.

Monitor the animal for potential complications: Esophagitis (inflammation of the oesophagus), perforation of the oesophagus or trachea, damage to the cardiac sphincter (upper stomach sphincter) insertion of needle and solution into the lungs, lung perforation, damage to the oral cavity, aspiration of solution into the lungs from regurgitation, traumatic injuries related to improper restrain.

Results

Safety Data:

No presence of aggressive behaviour, neither evident clinical alterations, such as presence of tremors, were observed in the experimental groups. One mouse in G4 showed immediate clinical signs of asphyxia after administration of the compound. This was found to be the consequence of an erroneous insertion of needle and solution into the lungs and the mouse was excluded from the experiments.

Figure 4:
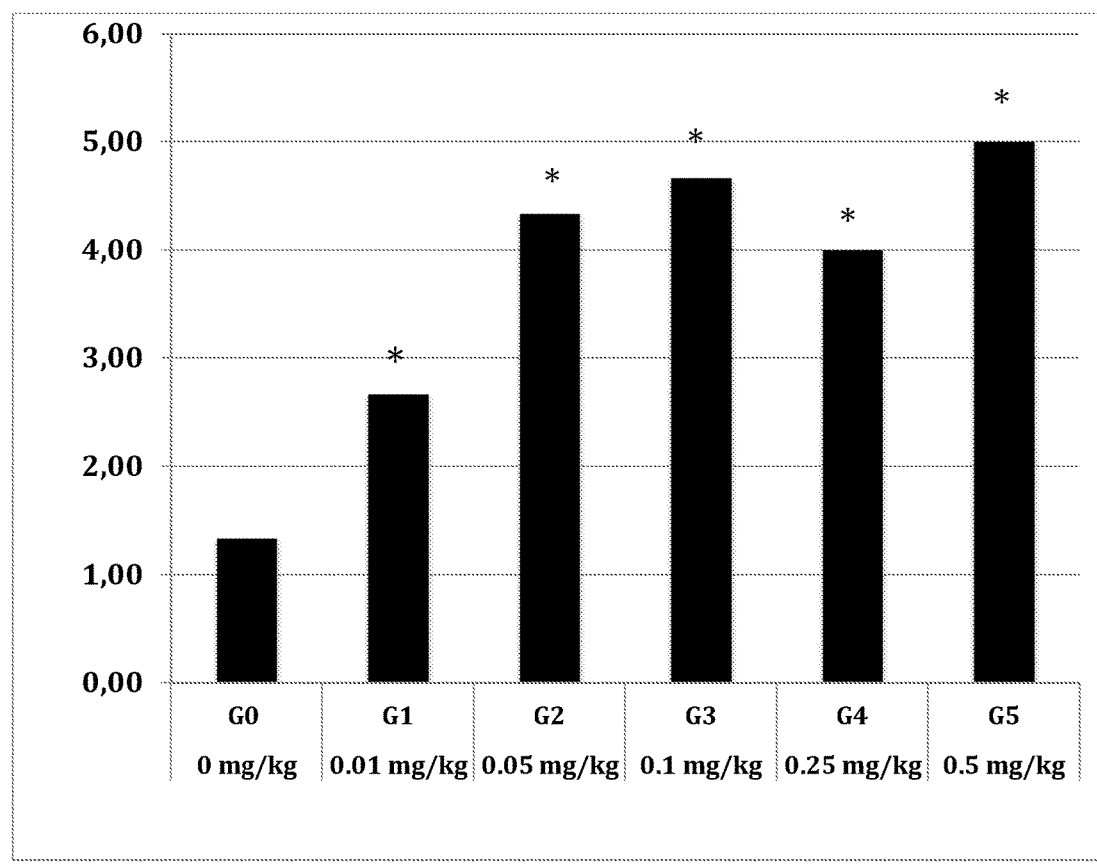
FIG. 4 shows a graphical representation of the mean number of mice sleeping with each group 30 minutes following single administration of the compound according to the invention at 3 consecutive days.

Sleep Monitoring:

The graphical representation of the mean number of mice sleeping within each group 30 minutes following single administration of the compound at 3 consecutive days is shown in FIG. 4. All 5 doses tested increased significantly the number of mice sleeping 30 minutes after administration of Cannabinol at 3 consecutive days. This indicates that the liquid oral formulation in olive oil can be used to enhance sleep.

Body Weight:

No significant changes of body weight within experimental groups with time or among experimental groups at fixed time were observed.

Organ Weight:

The mean weights (and standard deviations) of spleen, liver and kidney from all mice groups at sacrifice are monitored. No significant changes in liver and kidney weights were observed among experimental groups.

REFERENCES

1. *Cannabis* and Man, Psychological and Clinical Aspects and Patterns of Use, Edited by P. H. Connell and N. Dorn 1975; Marijuana Botany,
2. The propagation and breeding of distinctive *cannabis* by Robert Connell Clarke, 1981
3. Booth M: *Cannabis*: A History. New York, N.Y.: St Martin's Press, 2003.
4. Adams I B, Martin B R: *Cannabis*: pharmacology and toxicology in animals and humans. Addiction 91 (11): 1585-614, 1996. [PUBMED Abstract]
5. Grotenhermen F, Russo E, eds.: *Cannabis* and Cannabinoids: Pharmacology, Toxicology, and Therapeutic Potential. Binghamton, N.Y.: The Haworth Press, 2002.
6. National Toxicology Program NTP toxicology and carcinogenesis studies of 1-trans-delta (9)-tetrahydrocannabinol (CAS No. 1972-08-3) in F344 rats and B6C3F1 mice (gavage studies). Natl Toxicol Program Tech Rep Ser 446 ( ): 1-317, 1996. [PUBMED Abstract]
7. Bifulco M, Laezza C, Pisanti S, et al.: Cannabinoids and cancer: pros and cons of an antitumour strategy. Br J Pharmacol 148 (2): 123-35, 2006. [PUBMED Abstract]
8. Sánchez C, de Ceballos M L, Gomez del Pulgar T, et al.: Inhibition of glioma growth in vivo by selective activation of the CB(2) cannabinoid receptor. Cancer Res 61 (15): 5784-9, 2001. [PUBMED Abstract]
9. McKallip R J, Lombard C, Fisher M, et al: Targeting CB2 cannabinoid receptors as a novel therapy to treat malignant lymphoblastic disease. Blood 100 (2): 627-34, 2002. [PUBMED Abstract]
10. Casanova M L, Blázquez C, Martinez-Palacio J, et al.: Inhibition of skin tumor growth and angiogenesis in vivo by activation of cannabinoid receptors. J Clin Invest 111 (1): 43-50, 2003. [PUBMED Abstract]
11. Blázquez C, González-Feria L, Alvarez L, et al.: Cannabinoids inhibit the vascular endothelial growth factor pathway in gliomas. Cancer Res 64 (16): 5617-23, 2004. [PUBMED Abstract]
12. Guzmán M: Cannabinoids: potential anticancer agents. Nat Rev Cancer 3 (10): 745-55, 2003. [PUBMED Abstract]
13. Blázquez C, Casanova M L, Pianas A, et al.: inhibition of tumor angiogenesis by cannabinoids. FASEB J 17 (3): 529-31, 2003. [PUBMED Abstract]
14. Vaccani A, Massi P, Colombo A, et al.: Cannabidiol inhibits human glioma cell migration through a cannabinoid receptor-independent mechanism. Br J Pharmacol 144 (8): 1032-6, 2005. [PUBMED Abstract]
15. Ramer R, Bublitz K, Freimuth N, et al.: Cannabidiol inhibits lung cancer cell invasion and metastasis via intercellular adhesion molecule-1. FASEB J 26 (4): 1535-48, 2012. [PUBMED Abstract]
16. Velasco G, Sánchez C, Guzmán M: Towards the use of cannabinoids as antitumour agents. Nat Rev Cancer 12 (6): 436-44, 2012. [PUBMED Abstract]
17. Torres S, Lorente M, Rodriguez-Furnès F, et al.: A combined preclinical therapy of cannabinoids and ternozolomide against glioma. Mol Cancer Ther 10 (1): 90-103, 2011. [PUBMED Abstract]
18. Vara D, Salazar M, Olea-Herrero N, et al.: Anti-tumoral action of cannabinoids on hepatocellular carcinoma; role of AMPK-dependent activation of autophagy. Cell Death Differ 18 (7): 1099-111, 2011. [PUBMED Abstract]
19. Preet A, Qamri Z, Nasser M W, et al.: Cannabinoid receptors, CB1 and CB2, as novel targets for inhibition of non-small cell lung cancer growth and metastasis. Cancer Prev Res (Phila) 4 (1): 65-75, 2011. [PUBMED Abstract]
20. Nasser M W, Qamri Z, Deol Y S, et al.: Crosstalk between chemokine receptor CXCR4 and cannabinoid receptor CB2 in modulating breast cancer growth and invasion. PLoS One 6 (9): e23901, 2011. [PUBMED Abstract]
21. Shrivastava A, Kuzontkoski P M, Groopman J E, et al.: Cannabidiol induces programmed cell death in breast cancer cells by coordinating the cross-talk between apoptosis and autophagy. Mol Cancer Ther 10 (7): 1161-72, 2011, [PUBMED Abstract]
22. Aviello G, Romano B, Borrelli F, et al.: Chemopreventive effect of the non-psychotropic phytocannabinoid cannabidiol on experimental colon cancer. J Mol Med (Berl) 90 (8): 925-34, 2012. [PUBMED Abstract]
23. Preet A, Ganju R K, Groopman J E: Delta9-Tetrahydrocannabinol inhibits epithelial growth factor-induced lung cancer cell migration in vitro as well as its growth and metastasis in vivo. Oncogene 27 (3): 339-46, 2008. [PUBMED Abstract]
24. Zhu L X, Sharma S, Stolina M, et al.: Delta-9-tetrahydrocannabinol inhibits antitumor immunity by a CB2 receptor-mediated, cytokine-dependent pathway. J Immunol 165 (1): 373-80, 2000 [PUBMED Abstract]
25. McKallip R J, Nagarkatti M, Nagarkatti P S: Delta-9-tetrahydrocannabinol enhances breast cancer growth and metastasis by suppression of the antitumor immune response. J Immunol 174 (6): 3281-9, 2005. [PUBMED Abstract]
26. Massa F, Marsicano G, Hermann H, et al.: The endogenous cannabinoid system protects against colonic inflammation. J Clin Invest 113 (8): 1202-9, 2004, [PUBMED Abstract]
27. Patsos H A, Hicks D J, Greenhough A, et al.: Cannabinoids and cancer: potential for colorectal cancer therapy. Biochem Soc Trans 33 (Pt 4): 712-4, 2005. [PUBMED Abstract]
28. Liu W M, Fowler D W, Dalgleish A G: *Cannabis*-derived substances in cancer therapy—an emerging anti-inflammatory role for the cannabinoids. Curr Clin Pharmacol 5 (4): 281-7, 2010. [PUBMED Abstract]
29. Malfitano A M, Ciaglia E, Gangemi G, et al.: Update on the endocannabinoid system as an anticancer target. Expert Opin Ther Targets 15 (3): 297-308, 2011. [PUBMED Abstract]
30. Sarfaraz S, Adhami V M, Syed D N, et al.: Cannabinoids for cancer treatment: progress and promise. Cancer Res 68 (2): 339-42, 2008. [PUBMED Abstract]
31. Mechoulam R, Berry E M, Avraham Y, et al.: Endocannabinoids, feeding and suckling—from our perspective. Int J Obes (Lond) 30 (Suppl 1): S24-8, 2006. [PUBMED Abstract]
32. Fride E, Bregman T, Kirkham T C: Endocannabinoids and food intake: newborn suckling and appetite regulation in adulthood. Exp Biol Med (Maywood) 230 (4): 225-34, 2005. [PUBMED Abstract]
33. Walker J M, Hohmann A G, Martin W J, et al.: The neurobiology of cannabinoid analgesia. Life Sci 65 (6-7): 665-73, 1999. [PUBMED Abstract]

34. Meng I D, Manning B H, Martin W J, et al.: An analgesia circuit activated by cannabinoids. Nature 395 (6700): 381-3, 1998. [PUBMED Abstract]
35. J M, Huang S M, Strangman N M, et al.: Pain modulation by release of the endogenous cannabinoid anandamide. Proc Natl Acad Sci USA 96 (21): 12198-203, 1999. [PUBMED Abstract]
36. Facci L, Dal Toso R, Romanelio S, et al.: Mast cells express a peripheral cannabinoid receptor with differential sensitivity to anandamide and palmitoylethanolamide. Proc Natl Acad Sci USA 92 (8): 3376-80, 1995. [PUBMED Abstract]
37. Ibrahim M M, Porreca F, Lai J, et al.: CB2 cannabinoid receptor activation produces antinociception by stimulating peripheral release of endogenous opioids. Proc Natl Acad Sci USA 102 (8): 3093-8, 2005. [PUBMED Abstract]
38. Richardson J D, Kilo S, Hargreaves K M: Cannabinoids reduce hyperalgesia and inflammation via interaction with peripheral CB1 receptors. Pain 75 (1): 111-9, 1998. [PUBMED Abstract]
39. Khasabova I A, Gielissen J, Chandiramani A, et al.: CB1 and CB2 receptor agonists promote analgesia through synergy in a murine model of tumor pain. Behav Pharmacol 22 (5-6): 607-16, 2011. [PUBMED Abstract]

The invention claimed is:

1. A method of treating attention deficit hyperactivity disorder or chronic insomnia in a human in need thereof consisting essentially of administering a therapeutically effective amount of pure cannabinol to said human in need thereof to effectively treat the attention deficit hyperactivity disorder or chronic insomnia in the human in need thereof, wherein said pure cannabinol is obtained by isolation and purification from a natural source or by synthetic means.

2. The method of claim 1, which treats attention deficit hyperactivity disorder in a human in need thereof.

3. The method of claim 1, which treats chronic insomnia in a human in need thereof.

4. The method of claim 1, wherein said pure cannabinol is obtained by synthetic means.

5. The method of claim 1, wherein said pure cannabinol is obtained by isolation and purification from a natural source.

6. The method of claim 1, wherein the administration is in the form of a powder, tablet or liquid.

* * * * *